United States Patent [19]

Choi et al.

[11] Patent Number: 5,587,167
[45] Date of Patent: Dec. 24, 1996

[54] PHARMACEUTICAL COMPOSITION FOR PROPHYLAXIS AND TREATMENT OF PREMATURE EJACULATION

[76] Inventors: Hyung K. Choi, 10-71, Sambu Apt., Yoido-dong, Youngdeungpo-gu, Seoul, Rep. of Korea; Zhong C. Xin, 5, Guiping Hutong, Beisan Street,Chuaying District, JiLin City, JiLin Province, China

[21] Appl. No.: 304,855

[22] Filed: Sep. 13, 1994

Related U.S. Application Data

[63] Continuation-in-part of Ser. No. 175,564, Dec. 30, 1993, abandoned.

[30] Foreign Application Priority Data

Sep. 14, 1993 [JP] Japan ..................... 93-18467

[51] Int. Cl.⁶ ............ A61K 35/56; A61K 35/78
[52] U.S. Cl. ..................... 424/195.1; 424/537
[58] Field of Search ................. 424/195.1, 537

[56] References Cited

U.S. PATENT DOCUMENTS 5,059,603  10/1991  Rubin ..................... 514/264
5,256,652  10/1993  El-Rashidy ............... 514/58

FOREIGN PATENT DOCUMENTS 1049454  2/1991  China .
1063223  8/1992  China .
1065206  10/1992  China .
1071453  4/1993  China .

OTHER PUBLICATIONS

Gould Medical Dictionary, 4th Ed., 1979, McGraw–Hill, New York.

The Collection of Traditional Chinese Prescriptions for Treating Sexual Problems, Changchun Printing Office 1992 p. 305.

Shi Zhi Chao et al., "The Collection of Traditional Chinese Prescriptions for Treating Sexual Problems," pp. 224, 305, Jun. 1992.

Primary Examiner—John W. Rollins
Assistant Examiner—Jean C. Witz
Attorney, Agent, or Firm—Birch, Stewart, Kolasch & Birch, LLP

[57] ABSTRACT

The present invention relates to an ointment composition for prophylaxis and treatment of premature ejaculation in a male patient and more particularly to a composition for applying to the glans penis, which contains the alcohol and/or aqueous extracts of ginseng radix, angelicae gigantis radix, broomrape, cassiae cortex, asiasari radix and bufonis venenum as the essential galenic components and, if necessary, one or more additional components selected from the extracts of xanthoxyli fructus, cnidium fructus, caryophylli flos and moschus.

14 Claims, No Drawings

PHARMACEUTICAL COMPOSITION FOR PROPHYLAXIS AND TREATMENT OF PREMATURE EJACULATION

CROSS-REFERENCE TO RELATED APPLICATION

This application is a continuation-in-part of U.S. patent application Ser. No. 08/175,564 filed Dec. 30, 1993, now abandoned.

BACKGROUND OF THE INVENTION

1. Field of the Invention

The present invention relates to a pharmaceutical composition for the prophylaxis and treatment of premature ejaculation. More particularly, the present invention relates to a galenic composition for the prophylaxis and treatment of male ejaculation accommodation ataxia due to sexual nervous hypersensitivity and to a process for preparing said galenic composition.

2. Background Art

The nervous system of the human body can be classified into the central nervous system and the peripheral nervous system. Nervous hypersensitivity (neuroticism) is generally caused by a disorder of the physico-neurological system which is under the influence of the central nervous system. However, sexual nervous hypersensitivity is mainly caused by a disorder in the complex cooperation between the peripheral nervous system and the central nervous system. Meanwhile, with the advance of modern civilization and the development of scientific technique an activation of the central nervous system is preferentially necessary for achieving high mental activities, such as the adaptation to novel scientific techniques, maintenance of smooth human relations and to maintain social discipline rather than to pursue the instinctive physical satisfaction in, for example, the necessities of life and sexual desire.

Such complicated social life results in a destruction of the balance and smooth cooperation of the central nervous system and peripheral nervous system. Particularly, in men, this may cause a loss of the ability to achieve sexual accommodation which is necessary for the satisfaction of the human instinctive desire. Recently, it has been determined that the number of cases manifesting various symptoms caused by such loss of sexual accommodation is rather large.

According to statistics, it has been shown that although there are some differences between age groups, approximately 30 to 50% of Korean adult men visiting impotence clinics suffer from sexual hypersensitivity. The typical example of sexual hypersensitivity is premature ejaculation, which is the main reason for sexual problems and which leads to social difficulties, such as asthenia due to the loss of self-confidence, as well as domestic discord. Premature ejaculation is defined as persistent or recurrent ejaculation before, upon, or shortly after penetration.

The reasons for premature ejaculation are generally thought to include a malfunction of the repressor center due to the fatigue of nervous transmission, hypersensitivity of a specific site due to genital disorders, hormonal disorders, physical problems and the like. It is believed that the premature ejaculation is generally caused by a complex interaction of the above mentioned reasons or by a loss of cooperation among the related sexual nerve centers.

Premature ejaculation has been treated with psychotherapy and drug therapy. Psychotherapy requires sexual training for a long period of time which involves discussions and cooperation with a physician and the patient and his wife. However, since psychotherapy necessitates a long period of time for the doctor, patient and his wife to work together in order to be effective, its success rate is low. That is, changes in living style, external stress, etc., undermine its success such that the problem either never is solved or it reoccurs. Therefore, drug therapy is now more widely used since time restrictions are not as great.

Present drug therapy includes psychotropic agents which suppress the excitation of the sexual nerve center and local anesthetics for blunting the sensitivity of the sexual peripheral nerve. However, since the central nervous system depressants may make the sexual act itself impossible due to a loss of sexual desire and since local anesthetics, such as lidocaine ointment or spray, sometimes induce vasoconstriction which may lead to transient erectile failure, and should be applied just before the sexual act because of its short duration, present day drug therapy cannot successfully solve the problems concerned with premature ejaculation.

Thus, the present inventors have extensively investigated the available literature and have continuously conducted studies and experiments related to overcoming the problem of premature ejaculation. As a result, the inventors have found that a suitable combination of certain galenic substances can provide an excellent pharmacological effect to overcome premature ejaculation without any of the problems associated with the prior therapeutic methods or drugs as mentioned above.

Therefore, it is an object of the present invention to provide a pharmaceutical galenic composition for the prophylaxis and treatment of premature ejaculation.

A further object of the present invention is to provide a pharmaceutical composition suitable for prophylaxis and treatment of premature ejaculation, which contains effective amounts of: extracts of ginseng radix, angelicae gigantis radix, broomrape, cassiae cortex, asiasari radix and bufonis venenum as the essential components.

A further object of the present invention is to provide a pharmaceutical composition for the prophylaxis and treatment of sexual hypersensitivity, which further contains one or more additional galenic substance selected from the group consisting of: extracts of xanthoxyli fructus, cnidium fructus, caryophylli flos and moschus, in addition to effective amounts of: extracts of ginseng radix, angelicae gigantis radix, broomrape, cassiae cortex, asiasari radix and bufonis venenum as the essential components.

A further object of the present invention is to provide a process for the preparation of said pharmaceutical composition for the prophylaxis and treatment of premature ejaculation.

A further object of the present invention is to provide a method for the prophylaxis and treatment of premature ejaculation.

The more pertinent and important features of the present invention have been outlined above in order that the detailed description of the invention which follows will be better understood and so that the present contribution to the art can be fully appreciated. Those skilled in the art can appreciate that the conception and the specific embodiments disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

DISCLOSURE OF INVENTION

In the pharmaceutical composition according to the present invention, ginseng radix, angelicae gigantis radix, broomrape, cassiae cortex, asiasari radix and bufonis venenum are used as the essential galenic components. In addition to the above essential components, the pharmaceutical composition of the present invention can preferably contain one or more additional galenic components selected from the group consisting of: moschus, xanthoxyli fructus, cnidium fructus and caryophylli flos.

Each of the raw galenic components used in the present invention exhibits certain pharmacological effects. Ginseng radix is used for its tonic, analeptic and sedative activities and for its fatigue amelioration and its effect of stimulating metabolism. Angelicae gigantis radix is generally used in the treatment of anemia and blood flow disorders in obstetrics and in gynecology for the purpose of blood supplementation and pain relief. Broomrape is effective for the enhancement of sexual desire and as an analeptic. In addition, cassiae cortex contains an essence component in a large amount, which exhibits peripheral vasodilating activity and also a stimulating effect in a small amount, but an inhibiting effect in a large amount, on the central nervous system, and is generally used as an analgesic, anticonvulsant and tonic agent. Asiasari radix contains an essence component which exhibits an antihistaminic effect and, therefore, is clinically used as an antipyretic, analgesic, antitussive and expectorant. Bufonis venenum is a substance secreted from the otic gland of toads which has cardiotonic, analeptic, diuretic, analgesic and detoxicating effects and also has a superior local anesthetic effect and vasodilating effect. In addition, xanthoxyli fructus has topical sensory paralysis activity and peripheral vasodilating activity and is clinically used as an analgesic and anticonvulsant. Moschus is a dry substance of musk pod secretions from musk deer and is widely used as an analeptic, cardiotonic, tonic, sedative, anticonvulsant, pus-removing and detoxicating agent in view of its tonic, analeptic, anti-inflammatory and beta-adrenergic effects. Further, both cnidium fructus and caryophylli flos possess analeptic and peripheral vasodilating effects.

The pharmaceutical composition of the present invention can be formulated in the form of ointments, pills, suspensions, gels or liquid formulations for topical application by a process which comprises either extracting with a solvent or pulverizing the galenic substances depending on the physico-chemical properties of their active components, combining the obtained extracts and/or powder, and then formulating the mixture into the desired formulations according to conventional methods known in the art of pharmacy.

Although the mechanism of pharmacological action of the composition of the present invention cannot be exactly identified, it is believed that the analgesic, sedative and anesthetic actions of the composition of the present invention may reduce or paralyze the sensory function of a hypersensitive glans receptor, which is the main portion of the ejaculation reflex nerve, and block the transfer pathway to the central nervous system to sedate the (sexual) exciting center, and at the same time, the blood flow-accelerating activity of the present composition may cause the erection to isolate the ejaculation reflex nerve from the sexual contact surface so that the hypersensitive sexual nerve cannot be stimulated, thereby preventing premature ejaculation. The above explanation is merely provided as one explanation of how the composition according to the present invention functions. However, the inventors do not want to be held to this explanation as being the only explanation of the mechanism of action.

More specifically, according to the present invention 60–140 parts by weight of ginseng radix, 60–140 parts by weight of angelicae gigantis radix, 60–140 parts by weight of broomrape, 10–30 parts by weight of cassiae cortex, 10–30 parts by weight of asiasari radix and 15–25 parts by weight of bufonis venenum as essential components can be appropriately treated and combined to prepare the desired pharmaceutical composition. Preferably, one or more additional galenic components selected from the group consisting of 40–70 parts by weight of xanthoxyli fructus, 60–140 parts by weight of cnidium fructus, 10–30 parts by weight of caryophylli flos and 5–15 parts by weight of moschus can be further incorporated into the pharmaceutical composition of the present invention.

The constitutional ratio of the galenic components as described above was established on the basis of the results obtained from numerous animal experiments. When the galenic components are combined in a ratio lower than the lowest level as defined above, the pharmacological effect of the corresponding components was drastically reduced. On the other hand, when any component is combined in a ratio higher than the highest level thereof, the effect of other components was reduced, and the synergistic and cooperative action of the composition of the present invention is significantly reduced. Therefore, it is critical that the galenic components of the composition of the present invention are combined in the ratio as defined above.

Among the raw galenic substances, ginseng radix, angelicae gigantis radix, broomrape, cnidium fructus and xanthoxyli fructus are used in the form of extracts obtained by extraction of the active components with alcohol or water. Cassiae cortex, caryophylli flos and asiasari radix are used by immersion in water and then concentrated. Bufonis venenum is used either in the form of a powder obtained by dissolving it in human milk and then concentrating it to dryness or in the form of an extract obtained by extraction of the active component with alcohol or water. Moschus is prepared as a dry powder or an alcohol extract. Said pretreated galenic substances can be uniformly mixed with pharmaceutically acceptable carriers to obtain the desired pharmaceutical composition for treating premature ejaculation according to the present invention.

In view of the nature of the indication, the composition of the present invention is most preferably administered in the form of a topical ointment. However, if necessary, the composition of the present invention can be prepared and stored in the form of a gel, suspension, solution, dispersion, spray or pill or in the form of a tablet, which may be converted into another formulation when the composition is used.

If the composition of the present invention is in the form of an ointment, it is preferable that about 0.1–0.5 g of the ointment be externally applied to a portion of glans penis 30 minutes to 10 hours before the expected initiation of sexual intercourse. Then in about 20 to 30 minutes after application the ointment may be washed off with water in order to remove any unpleasant feeling that may accompany the topical application. In 20 to 30 minutes after topical application genital hypersensitivity is dulled or blunted and blood flow is stimulated. The effect of the ointment lasts for about 8 to 12 hours.

The present invention will be more specifically illustrated by the following example and experiments. However, it should be understood that the present invention is not limited by these examples in any manner.

EXAMPLE 1

Ointment Preparation a) 100 g of ginseng radix, 100 g of angelicae gigantis radix, 100 g of broomrape, 100 g of cnidium fructus and 50 g of xanthoxyli fructus were washed with water, dried, ground, and then immersed in 2500 ml of 90% ethanol for 24 hours and filtered. The residue was again immersed in 2000 ml of 90% ethanol for 24 hours and filtered. The obtained two filtrates were combined and distilled to remove ethanol and to obtain the extract. The residue from the above ethanol extraction was immersed in 2500 ml of water for 4 hours at the temperature below 80° C. The extract was then filtered to remove the residue. The filtrate was immersed in 2500 ml of 95% ethanol for 24 hours under cooling. The mixture was filtered to remove the precipitated substance. The filtrate was distilled to remove ethanol and then combined with the alcohol extract obtained above. The combined extract was concentrated under reduced pressure to 1000 ml, and 10 g of active carbon was added thereto. The mixture was warmed to 80° C. for 30 minutes and then filtered. The filtrate was concentrated at a temperature below 80° C. under reduced pressure and then lyophilized to obtain about 100 g of the extract powder.

b) 20 g of cassiae cortex, 20 g of caryophylli flos and 20 g of asiasari radix were cleaned by washing with water, immersed in 300 ml of distilled water for 4 hours and then doubly distilled to obtain about 5 g of the extract comprising the essence components.

c) 20 g of bufonis venenum was immersed in 1000 ml of 70% ethanol at 50° C. for 4 hours and then filtered. The filtrate was distilled to remove ethanol. The filter cake was immersed again in 500 ml of distilled water at 50° C. for 4 hours and then filtered. The filtrate was combined with the previously obtained filtrate, and 5 g of active carbon was added thereto. The mixture was warmed at 80° C. for 30 minutes and filtered. The filtrate was concentrated under reduced pressure at a temperature below 50° C and then lyophilized to obtain 5 g of a powder.

d) 10 g of moschus was immersed in 500 ml of 70% ethanol at 50° C for 4 hours and filtered. The filtrate was distilled to remove ethanol. The filter cake was immersed again in 300 ml of distilled water at 50° C. for 4 hours and then filtered. The filtrate was combined with the previously obtained filtrate, and 3 g of active carbon were added thereto. The mixture was warmed to 80° C. for 30 minutes and filtered. The filtrate was concentrated under reduced pressure at a temperature below 50° C. and then lyophilized to obtain 2 g of a powder.

The powders obtained in a), c) and d) above were mixed uniformly with the essence obtained in b) above. Then the mixture was uniformly mixed with polyethylene glycol as water-soluble base in a ratio of 1:9 by weight to prepare a yellow colored ointment composition according to the present invention.

EXPERIMENT 1

Test for Toxicity and Side Effects a) About 0.2 g of the ointment prepared in above EXAMPLE 1 was applied five (5) times at an interval of 10 minutes to the glans penis of each of 5 adult male rabbits and then the appearance of the penis was observed every hour for 12 hours. Then the ointment was washed off the penis of each rabbit and the appearance of the penis was observed every 30 minutes for 10 hours. As a result, a hyperemia due to the genital vasodilation continuously remained from one hour after the ointment of the present invention was applied, and then remained for about 10 hours even after removal of the ointment. Thereafter, the hyperemia gradually disappeared. However, the application of the ointment of the present invention did not cause any denaturation of the genital epidermis or any histological change and also, any functional disorder was observed.

b) The present inventors have determined a suitable dosage and a method of use by topically applying the ointment according to the present invention to themselves on several different occasions. As a result of this, they determined that dosage for a single application to obtain the desired effect is about 0.1 to 0.2 g of the ointment applied to the glans of the penis. The ointment was applied three times with 0.2 g of the ointment being applied at each application at an interval of 30 minutes apart. The ointment was allowed to remain for 10 hours before being washed off. As a result, a topical or systemic side effect, except for a topical burning sensation due to vasodilation, could not be identified. Said topical burning sensation disappeared after 30 minutes in accordance with the blunting of the sense in glens portion of the penis.

EXPERIMENT 2

Clinical Test a) This clinical test was conducted for 30 patients with informed consent, who suffer from serious sexual disorders due to premature ejaculation and who agreed with this clinical trial schedule at the Yongdong Severance Hospital, Urology Department, residing in Kangnam-ku, Seoul, Korea, under surveillance of the present inventors with the ointment prepared in the above EXAMPLE 1 according to the present invention. The age of the subject patients was in the range of 32 to 57 and the period of the sexual functional disorder was 3 months to 30 years. Those patients were divided into 15 patients suffering from simple premature ejaculation and 15 patients suffering from premature ejaculation and accompanying erection failure. None of the subject patients showed any hormonal disorder or abnormality in physico-chemical examination. According to the audio-visual stimulating test (AVS-Penogram) using a radio-isotope (Technetium$^{99m}$-RBC), the patients were classified into a group of 14 patients showing normal dynamic change in penis blood flow (Type I) and a group of 16 patients showing abnormal change in penis blood flow (Type II). The main etiological factor in those patients was determined as psychogenic. The subject patients included 2 patients who have never improved their premature ejaculation even after implantation of a penile prosthesis, and 20 patients who did not show any effect with a commercial local anesthetic spray.

The patient was instructed to uniformly apply the ointment of the present invention to the penis glans in an amount of 0.2 g each time sexual intercourse was anticipated. Then the ointment was to be washed off after 20 to 30 minutes. Thereafter, the patients were advised to have sexual intercourse within 2 to 8 hours and report the ejaculation accomodation ability every week. The ejaculation accommodation ability of the ointment of the present invention was estimated by examining the change in time from the initiation of the sexual act to the ejaculation, and conjugal satisfaction feeling through 4 times of monitoring at an interval of one week. As a result, in the patients having simple premature ejaculation, the ejaculation time was extended from not more than 2 minutes before the use of the ointment according to the present invention, to 15 to 20 minutes after the use of the ointment. In the group of patients suffering from erection failure and premature ejaculation it was reported that as well as premature ejaculation, the erection state was somethat improved. Before use of the ointment, 13 severe patients ejaculated just before or just after vaginal penetration, 12 patients ejaculated within one minute just after penetration, and 5 patients ejaculated within 2 minutes after penetration. However, at the time of first report after one week from use of the ointment, the delay in ejaculation time increased to 10 minutes in 2 patients, 15 minutes in 13 patients and more than 20 minutes in 13 patients. Two (2) patients, including one suffering from chronic prostatitis, showed little increase in the delay in ejaculation time from just after the sexual act to 2 minutes and 5 minutes, respectively. In addition, at the time of the third report it was determined that the ejaculation time was extended to 15 minutes in 2 patients and 20 minutes in 26 patients, except for the non-effected 2 patients. Thereafter, 11 of the above patients reported that a satisfactory sexual act is possible without using the ointment of the present invention, but the remaining patients could not be monitored any longer.

b) The effect of the composition of the present invention was compared with that of a commercial lidocaine cream. This comparative test was conducted for 50 volunteer patients, with an average age of 41.4, who suffer from premature ejaculation due to genital hypersensitivity and visit the Yongdong Severance Hospital. In this test, the ointment prepared in EXAMPLE 1 of the present invention, 1.5% lidocaine cream, 5% lidocaine cream, 10% lidocaine cream and a placebo were designated SS, LL, ML, HL and PB, respectively, so that the patients could not know the drug used. The patients were advised to externally apply the 5 kinds of drugs, in order, to the penis and then have sexual intercourse. That is, each of the lidocaine creams and the placebo was applied in an amount of 0.2 g before 30 minutes to one hour from sexual intercourse and the ointment according to the present invention was applied in an amount of 0.2 g before 1 to 8 hours from sexual intercourse. Then each of the tested drugs was washed off after 30 minutes. Thereafter, the patients were instructed to report the lasting time of sexual intercourse and the sex satisfaction after one month. Among the 50 volunteer patients, 43 patients submitted the reports within one to three months after the beginning of the test. The average value of the obtained results is described in the following table.

| Tested drug | Lasting time of sexual intercourse (min.) | Sex satisfaction[1] (number of patients) | | | | Remarks |
|---|---|---|---|---|---|---|
| | | A | B | C | D | |
| Before use | 0.8 | 43 | 0 | 0 | 0 | |
| PB | 1.3 | 40 | 3 | 0 | 0 | |
| LL | 1.9 | 38 | 5 | 0 | 0 | |
| ML | 2.2 | 36 | 7 | 0 | 0 | |
| HL | 3.7 | 30 | 8 | 3 | 2 | (2) |
| SS | 11.3 | 2 | 4 | 25 | 12 | |

Note:
[1]A = dissatisfied
B = usual
C = satisfied
D = very satisfied
[2]11 patients suffer from genital insensability and erection disorder.

EXPERIMENT 3

Test for Effect of Stimulating the Blood Circulation

The temperatures of the penis and scrotum of 10 normal volunteers were measured by means of Computerized Infrared Thermography Imaging. The ointment prepared in the above EXAMPLE 1 according to the present invention was applied to the penis of each volunteer in an amount of 0.2 g and then the temperatures of the penis and scrotum were measured for 8 hours at an interval of 2 hours by means of the same method. As a result, it could be determined that the topical temperature of the penis and scrotum continuously increased by about 0.8°–1.1° C. from an average of 27.5° C. before use of the ointment to an average of 28.5° C. Thus, it is shown that the ointment of the present invention stimulates the blood circulation at the genital portion including the penis and scrotum.

EXPERIMENT 4

Test for Local Anesthetic Effect

This test was conducted for 20 patients who suffer from premature ejaculation due to sexual nervous hypersensitivity and visit the Yongdong Severance Hospital, Urology Department. The average age of the patients was 39.5 years, the average marriage period was 13.8 years, and the average duration of premature ejaculation was 15.7 years. Among the patients, 15 patients suffered from simple premature ejaculation and 5 patients suffered from premature ejaculation accompanying erection failure. In all the patients the results of physico-chemical examination and neurological examination were normal. The specific test method is described below.

The patients were in a supine position and their eyes were covered up. The examiner randomly stimulated glans penis, scrotum and perineum with a cotton thread so that the patients themselves can identify their stimulating portion. The patients who can accurately identify the touch feeling at all these stimulating portions were selected for this test to record the test results. Using biothesiometry, an electrode was attached to each of the index finger, glans penis, scrotum and perineum and then the voltage was slowly increased until the patients feel the sense of vibration. The value of the meter at which the patients feel the sense of vibration was recorded. This test was practiced three times. The lowest value as obtained was selected as the standard. Thereafter, 0.2 g of the ointment prepared in EXAMPLE 1 of the present invention was applied to the glans penis and then the above test procedure was practiced again to record the result.

According to this test, although the patients can identify the touch feeling at all the portions of the index finger, glans penis, scrotum and perineum stimulated by a cotton thread before application of the ointment of the present invention, after one hour from application of the ointment of the present invention the touch feeling with the cotton thread at the glans penis disappeared in all the patients and no change in any other portions was observed. Before application of the ointment of the present invention, the average vibration sense measured by biothesiometry was 0.04 microns in the index finger, 0.05 microns in the glans penis, 0.08 microns in the scrotum and 0.57 microns in the perineum. One hour after application of the ointment of the present invention, the vibration sense of the glans penis was determined as 0.10 microns, which is double the value measured before the ointment application, and no remarkable change in other portions was observed.

| Measured portions | Value measured by biothesiometry | |
|---|---|---|
| | Before ointment application | After ointment application |
| index finger | 0.04 microns | 0.04 microns |
| glans penis | 0.05 microns | 0.10 microns |
| scrotum | 0.08 microns | 0.08 microns |
| perineum | 0.57 microns | 0.56 microns |

From the above results, it can be determined that the ointment of the present invention has activity in blunting topical touch feeling and topical vibration sense, which is believed to be the main mechanism for treatment of preamture ejaculation due to genital hypersensitivity.

From the results of the clinical trials above, it has been shown that since the composition of the present invention is composed of the galenic components, it has no side effect and that the time for use of the present composition can be freely selected due to its long lasting effect. Furthermore, it is apparent that the composition of the present invention is suitable for satisfactory sexual life since it provides an effect of treating premature ejaculation and further of stimulating blood circulation, and therefore is somewhat useful for improving erection failure.

Although this invention has been described in its preferred form with a certain degree of particularity, it is appreciated by those skilled in the art that the present disclosure of the preferred form has been made only by way of example and that numerous changes in the details of the construction, combination and rearrangement of parts may be resorted to without departing from the spirit and scope of the invention.

What is claimed is:

1. A topical pharmaceutical composition for treatment of premature ejaculation, comprising a member selected from the group consisting of a dried alcohol extract, an aqueous extract, and a combination of a dried alcohol extract and an aqueous extract of 60 to 140 parts by weight raw ginseng radix, 60 to 140 parts by weight angelicae gigantis radix, 60 to 140 parts by weight broomrape, 10 to 30 parts by weight cassiae cortex, 10 to 30 parts by weight asiasari radix, 60 to 140 parts by weight cnidium fructus, 40 to 70 parts by weight xanthoxyli fructus, 10 to 30 parts by weight caryophylli flos and 15 to 25 parts by weight bufonis venenum, and a pharmaceutically acceptable carrier, adjuvant or excipient therefor.

2. The topical pharmaceutical composition of claim 1, further comprising at least one component selected from the group consisting of a dried alcohol extract, an aqueous extract and a combination of a dry alcohol extract and an aqueous extract, and a combination of a dried alcohol extract and an aqueous extract of 5 to 15 parts by weight moschus.

3. The pharmaceutical composition of claims 1 or 2, wherein said composition is formulated in the form of an ointment, dispersion, suspension, gel, spray, or solution.

4. A process for the preparation of a pharmaceutical composition useful as an agent for treatment of premature ejaculation, which comprises forming an alcohol extract, an aqueous extract, or a combination of an alcohol extract and an aqueous extract of 60 to 140 parts by weight raw ginseng radix, 60 to 140 parts by weight angelicae gigantis radix, 60 to 140 parts by weight broomrape, 10 to 30 parts by weight cassiae cortex, 10 to 30 parts by weight asiasari radix, 60 to 140 parts by weight cnidium fructus, 40 to 70 parts by weight xanthoxyli fructus, 10 to 30 parts by weight caryophylli flos and 15 to 25 parts by weight bufonis venenum; and combining said alcohol extract, said aqueous extract, or said combination of an alcohol extract and an aqueous extract with a pharmaceutically acceptable ointment base.

5. The process of claim 4, further comprising including at least one component selected from the group consisting of an alcohol extract, an aqueous extract, and a combination of an alcohol extract and an aqueous extract of 5 to 15 parts by weight moschus.

6. The process of claim 4, wherein said ointment base is a water-soluble ointment base.

7. A method for the treatment of premature ejaculation in a male patient suffering from premature ejaculation, comprising applying 0.1 to 0.5 g of said pharmaceutical composition as defined in claims 1 or 2 to the glans penis of said male patient suffering from premature ejaculation.

8. The method of claim 7, wherein said pharmaceutical composition is applied 30 minutes to 10 hours before the expected initiation of sexual intercourse, and removed about to 30 minutes after application.

9. A process for the preparation of a pharmaceutical composition useful as an agent for treatment of premature ejaculation, comprising:

(1) washing with water, drying, and grinding 100 g of ginseng radix, 100 g of angelicae gigantis radix, 100 g of broomrape, 100 g of cnidium fructus, and 50 g of xanthoxyli fructus;

(2) immersing the ground material of step (1) in 2500 ml of 90% ethanol for 24 hours and then filtering to obtain a filtrate and a residue;

(3) immersing said residue of step (2) in 2000 ml of 90% ethanol for 24 hours and then filtering to obtain a filtrate and a residue;

(4) combining said filtrates of steps (2) and (3) and subjecting the combined filtrate to distillation to remove ethanol and obtain an extract;

(5) immersing said residue of step (3) in 2500 ml of water for 4 hours at a temperature below 80° C. to produce an extract;

(6) filtering said extract of step (5) to produce a filtrate and remove any residue;

(7) immersing said filtrate of step (6) in 2500 ml of 95% ethanol to produce a mixture, and cooling said mixture for 24 hours;

(8) filtering said mixture of step (7) to remove precipitated substances and produce a filtrate;

(9) distilling said filtrate of step (8) to remove ethanol and produce an extract;

(10) combining said extracts of steps (4) and (9) to produce a combined extract;

(11) concentrating said combined extract of step (10) under reduced pressure to produce a concentrated combined extract, and adding active carbon thereto;

(12) warming said concentrated combined extract of step (11) to 80° C. for 30 minutes and then filtering to produce a filtrate;

(13) concentrating said filtrate of step (12) under reduced pressure at a temperature below 80° C. and lyophilizing to obtain an extract powder;

(14) washing with water, and then immersing in distilled water for 4 hours and then doubly distilled water, 20 g of cassiae cortex, 20 g of caryophylli flos, and 20 g of asiasari radix, to obtain an essence;

(15) immersing 20 g of bufonis venenum in 1000 ml of 70% ethanol for 4 hours at 50° C. and then filtering to produce a filtrate and a filter cake;

(16) distilling said filtrate of step (15) to remove ethanol;

(17) immersing said filter cake of step (15) in 500 ml of distilled water for 4 hours at 50° C. and then filtering to produce a filtrate;

(18) combining said filtrate of step (15) and said filtrate of step (17) to produce a mixture, and adding active carbon thereto;

(19) warming said mixture of step (18) for 30 minutes at 80° C., and then filtering to produce a filtrate;

(20) concentrating said filtrate of step (19) under reduced pressure at a temperature below 50° C. and then lyophilizing to obtain a powder;

(21) immersing 10 g of moschus in 500 ml of 70% ethanol at 50° C. for 4 hours and then filtering to produce a filtrate and a filter cake;

(22) distilling said filtrate of step (21) to remove ethanol;

(23) immersing said filter cake of step (21) in 300 ml of distilled water at 50° C. for 4 hours and then filtering to produce a filtrate;

(24) combining said filtrates of steps (21) and (23) to produce a mixture, and adding active carbon thereto;

(25) warming said mixture of step (24) to 80° C. for 30 minutes and then filtering to produce a filtrate;

(26) concentrating said filtrate of step (25) under reduced pressure at a temperature below 50° C. and then lyophilizing to obtain a powder;

(27) mixing said powders of steps (13), (20), and (26) with said essence of step (14) to produce a mixture; and

(28) mixing said mixture of step (27) with polyethylene glycol in a ratio of 1:9 by weight to produce an ointment.

10. The ointment produced by the process of claim 9.

11. A method for the treatment of premature ejaculation in a male patient suffering from premature ejaculation, comprising applying 0.1 to 0.5 g of said ointment of claim 10 to the glans penis of said male patient suffering from premature ejaculation.

12. The method of claim 11, wherein 0.2 g of said ointment is applied to the glans penis of said male patient suffering from premature ejaculation.

13. The method of claim 11, wherein said ointment is applied 30 minutes to 10 hours before the expected initiation of sexual intercourse, and removed about 20 to 30 minutes after application.

14. The method of claim 12, wherein said ointment is applied 30 minutes to 10 hours before the expected initiation of sexual intercourse, and removed about 20 to 30 minutes after application.

* * * * *